United States Patent
Cohen et al.

(10) Patent No.: US 11,520,608 B1
(45) Date of Patent: Dec. 6, 2022

(54) METHOD AND SYSTEM FOR SELECTIVELY CLONING COMPUTER DISPLAY MONITORS

(71) Applicant: Biosense Webster (Israel) Ltd., Yokneam (IL)

(72) Inventors: Benjamin Cohen, Haifa (IL); Vladimir Dvorkin, Kiryat Motzkin (IL); Natan Sharon Katz, Atlit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/556,964

(22) Filed: Dec. 20, 2021

(51) Int. Cl.
| | |
|---|---|
| *G06F 3/14* | (2006.01) |
| *G06F 9/451* | (2018.01) |
| *G06F 3/147* | (2006.01) |
| *G16H 40/63* | (2018.01) |

(52) U.S. Cl.
CPC .............. *G06F 9/451* (2018.02); *G06F 3/147* (2013.01); *G06F 3/1423* (2013.01); *G06F 3/1454* (2013.01); *G16H 40/63* (2018.01)

(58) Field of Classification Search
CPC .... G06F 3/1454; G06F 3/1423; G06F 3/1438; G06F 3/1446; G06F 3/1462; G06F 3/147; G06F 9/451; G16H 40/63
See application file for complete search history.

(56) References Cited

U.S. PATENT DOCUMENTS

| | | | |
|---|---|---|---|
| 7,681,143 B2 | 3/2010 | Lindsay et al. | |
| 10,872,460 B1 * | 12/2020 | Luo | G06T 15/08 |
| 11,099,801 B2 * | 8/2021 | Sugumi | G16H 10/00 |
| 11,321,042 B2 * | 5/2022 | Sugumi | G06F 3/1446 |
| 2012/0289290 A1 | 11/2012 | Chae et al. | |
| 2013/0093738 A1 * | 4/2013 | Manus | G06F 3/1423 |
| | | | 345/204 |
| 2014/0325432 A1 | 10/2014 | Frederickson et al. | |
| 2021/0132687 A1 * | 5/2021 | Luo | G16H 30/20 |

* cited by examiner

*Primary Examiner* — Vijay Shankar
(74) *Attorney, Agent, or Firm* — Todd J. Burns

(57) ABSTRACT

A method for selectively cloning computer display monitors from a first one or more monitors associated with an operator, to a second one or more monitors associated with a surgeon includes: obtaining at least one configuration, such as a configuration file, that includes one or more Graphical User Interface (GUI) elements, such as windows, which are to be rendered to the second one or more monitors or not rendered to the second one or more monitors; analyzing the GUI elements displayed by the first one or more monitors against the at least one configuration for corresponding GUI elements; cloning corresponding GUI elements; and sending data representative of the cloned corresponding GUI elements to the second one or more monitors for display on the second one or more monitors. The method may also include displaying on the second one or more monitors the cloned corresponding GUI elements.

17 Claims, 3 Drawing Sheets

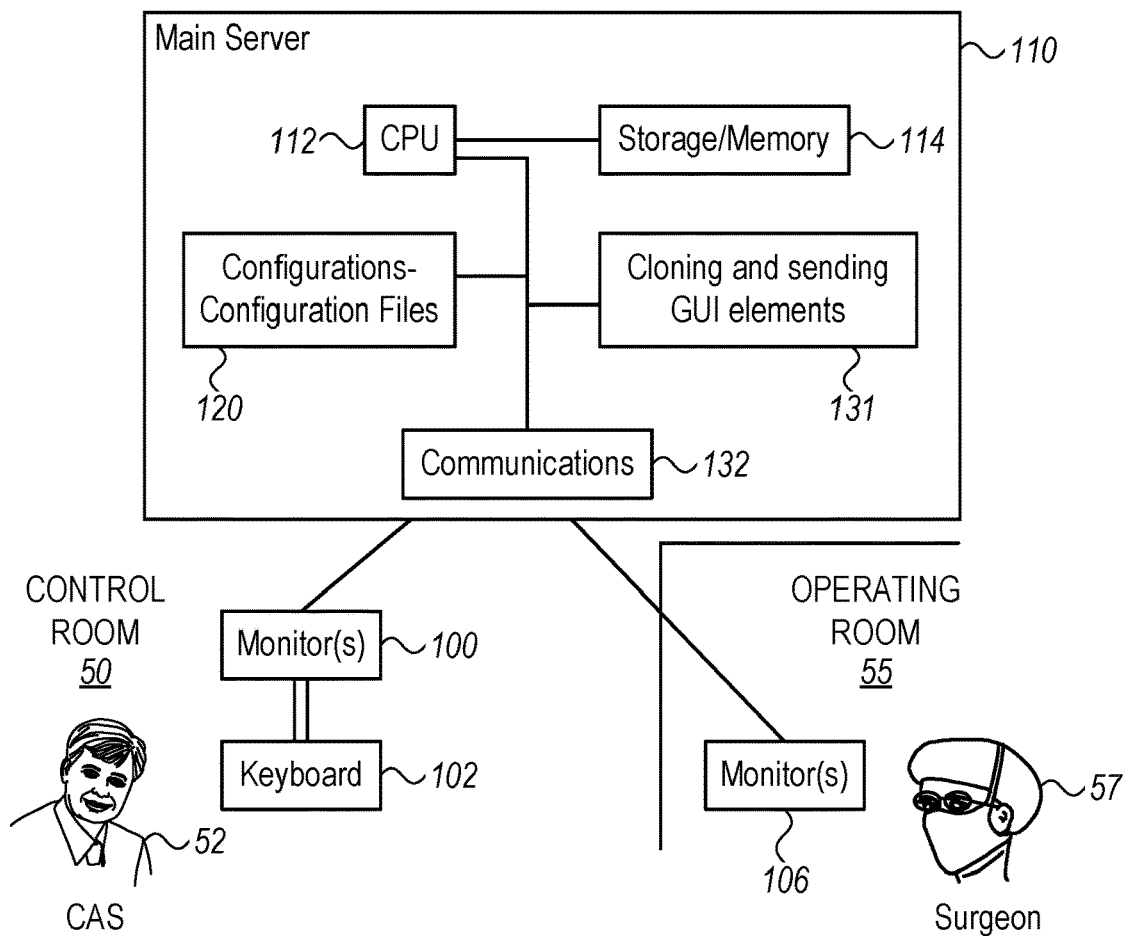
FIG. 1A
FIG. 1B
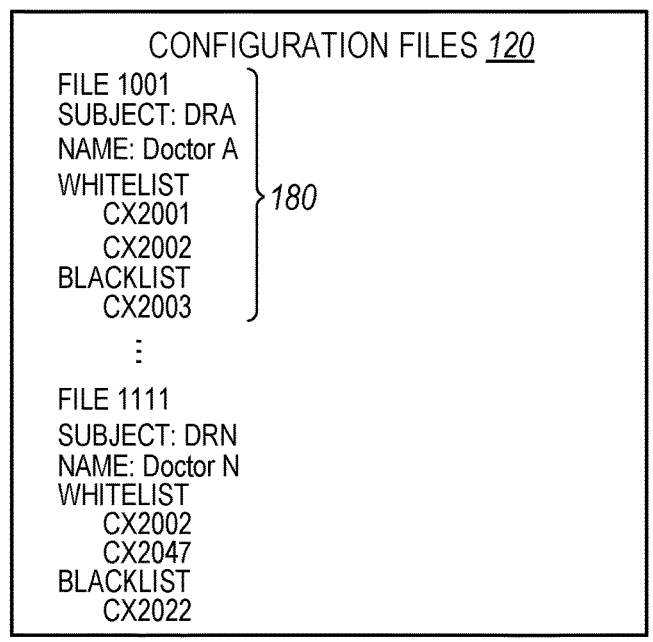

METHOD AND SYSTEM FOR SELECTIVELY CLONING COMPUTER DISPLAY MONITORS

TECHNICAL FIELD

The present disclosure relates generally to displays of the surgical field on monitors which assist the surgeon in performing the procedure, and particularly to methods and systems for selectively providing displays on display monitors.

BACKGROUND

As surgery becomes more advanced, surgeons are assisted by viewing the surgical field on monitors set up in the operating room. The views presented on these monitors may be controlled manually by a clinical account specialist (CAS), who is in a separate room, who manually selects and controls the views displayed to the CAS, which are the same views that the surgeon sees on the operating room monitors.

BRIEF DESCRIPTION OF THE DRAWINGS

The present disclosure will be more fully understood from the following detailed description of the examples thereof, taken together with the drawings in which:

FIG. 1A is an illustration of an example environment showing the disclosed subject matter;

FIG. 1B is a diagram of the database with configuration files, the data base from the main server of FIG. 1A, in accordance with an example of the disclosed subject matter;

DETAILED DESCRIPTION OF EXAMPLES

Figure 2:
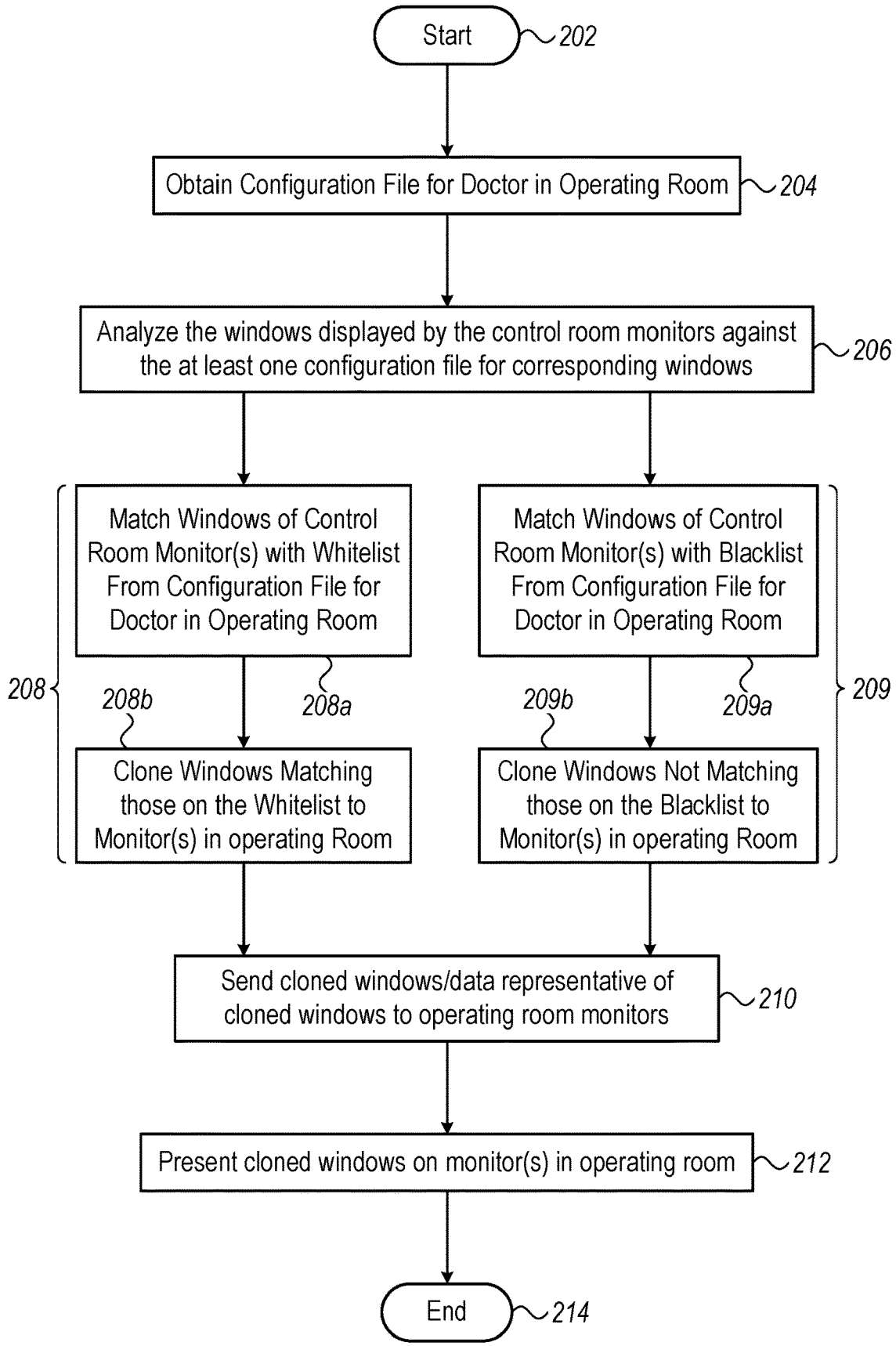
FIG. 2 is a flow diagram of example methods performed in accordance with the disclosed subject matter.

The present disclosed subject matter provides methods and systems which gives the clinical account specialist (CAS) control over the windows that the surgeon sees on the display monitors in the operating room. The CAS also knows which windows of a display are not being displayed in the operating room on the monitors.

Overview

Various surgical procedures involve displaying information to the surgeon on one or more monitors in the operating room. For example, some cardiac mapping procedures are performed to acquire, analyze, and display electroanatomical maps of the human heart, and provide real-time displays of catheter position superimposed on the 3D cardiac maps constructed. The 3D maps created are reconstructions based on the sampled point data during a procedure, As the points are added to the map, that particular mapped area is displayed on one or more screens or monitors.

The surgeon who performs the procedure normally assisted by a clinical account specialist (CAS) who controls the displays for the monitor(s) being used (viewed) by the surgeon. The CAS controls the monitors viewed by the surgeon, and typically the windows which the surgeon views on the surgeon's monitor(s).

While it is possible in principle to copy the exact views, e.g., windows open showing various views, charts and other graphics, on the monitor(s) of the CAS to the surgeon's monitor(s), the present disclosed subject matter allows for the monitor(s) of the CAS to be selectively cloned, copied, or otherwise duplicated, such that certain views, charts, and other graphics, for example, in the form windows, the windows corresponding to those in configuration file for the surgeon, are rendered to and displayed on the surgeon's monitor(s).

Selective cloning the views displayed to the surgeon is useful since, for example, some information may valuable to the CAS but meaningless to the surgeon. Unnecessary presentation of such information to the surgeon may distract his or her attention and/or obstruct information that is important. Selective cloninc enables tailoring the views presented to the CAS and the views presented to the surgeon according to the specific needs and preferences of each of them.

System Description

FIG. 1A shows an example environment, in which the disclosed subject matter operates. For example, the environment includes a control room 50 and an operating room 55, surgical theatre, or other clinical setting (collectively referred to hereinafter as an "operating room"), for example, typically in the same premises and close in distance to each other within the premises. An operator, in the present example a clinical operations specialist (CAS) 52 in the control room 50 views and controls the graphical user interface (GUI) elements, including, for example, windows, charts, toolbars, icons, and other graphical and/or visual elements, collectively referred to hereinafter as "GUI elements", being displayed on the one or more monitor(s) 100, for example, two monitors, via a keyboard 102, mouse, joystick, touch screen, or other control mechanism. A doctor (surgeon) 57, or other clinician or medical personnel, views the displayed windows on the one or more monitor(s) 106, for example two monitors, in the operating room 55.

The monitors 100 and key board 102 communicate with a main server 110, which is, for example, located in the control room 50, with communication by wired and/or wireless links, and, for example, by a direct connection. Alternately, the main server 110 may be in another room on the premises of the control room 50, where communication with the monitors 100 and keyboard 102 may be a direct connection or via local area networks, such as an enterprise network, or wide area networks, such as the Internet. In other alternatives, the monitors 100 and keyboard 102 may be in communication via local area networks, such as an enterprise network, or wide area networks, such as the Internet (not shown).

The monitors 106, depending on the location of the operating room 55 with respect to the main server 110, are in communication with the main server 110, for example, via the aforementioned direct connections or alternately via the local or wide area networks (not shown).

The main server 110 is of an architecture which includes one or more components, engines, modules and the like, for providing numerous functions and operations, and, for performing the disclosed processes. The main server 110 may be associated with additional storage, memory, caches and databases, both internal and external thereto.

The architecture of the main server 110 includes a central processing unit (CPU) 112 formed of one or more processors, electronically connected, i.e., either directly or indirectly, including in electronic and/or data communication with storage/memory 114, one or more databases of configurations, for example, in configuration files 120, a cloning and sending module 131, and a communications module 132. The aforementioned components 112, 114, 120, 131, 132 are in communication with each other, either directly or indirectly. While the main server 110 is shown as a single server, with all components 112, 114, 120, 131, 132 therein, the main server may be a plurality of servers and one or more of the components the components 112, 114, 120, 131, 132 may be outside of the main server 110, including along a network or in the cloud.

The Central Processing Unit (CPU) 112 is formed of one or more processors, including microprocessors, for performing the main server 110 functions and operations detailed herein, including accessing and/or controlling the configurations/configuration files 120, the cloning and sending module 131, and the communications module 132. The processors are, for example, conventional processors, including hardware processors such as those used in servers, computers, and other computerized devices.

The storage/memory 114 is any conventional storage media. The storage/memory 114 stores machine executable instructions for execution by the CPU 112, to perform the disclosed processes. The processors of the CPU 112 and the storage/memory 114, although shown as a single component for representative purposes, may be multiple components, and may be outside of the main server 110.

The configuration files 120, an example configuration of data, shown in detail in FIG. 1B, are used to configure initial parameters and initial settings for files used by the processes of the disclosed subject matter. The configurations files may be edited and new configuration files may be assed, for example, by system administrators or others with authorization or permissions to do so. These configuration files may, for example, be read every time the main server 110 starts up. For example, the configuration files shown are for each doctor (surgeon) and the windows which that doctor wants (e.g., a whitelist of windows), windows to be open and rendered, or does not want (e.g., a blacklist of windows), windows to be closed and not rendered, so as to appear on the monitors 106.

The cloning and sending module 131 is involved in the cloning, reproducing or otherwise duplicating of certain windows from the monitors 100 of the control room (and the CAS 52) for rendering and display on the monitors 106 of the operating room 55 (and the surgeon 57). The module 131, for example, via the communications module 132 sends the windows (data therefor) to the operating room monitors 106 of the windows which were cloned, for rendering thereon.

The communications module 132 facilitates communications between the main server 110 and the various computers, servers and the like, over various networks. For example, the communications module 110 facilitates communications over networks when an outside computer is communicating with the configuration filles database 120, to change or edit a configuration file, delete a configuration file or create a new configuration file.

Attention is now directed to FIG. 2, which show a flow diagram detailing computer-implemented processes in accordance with examples of the disclosed subject matter. Reference is also made to elements shown in FIGS. 1A and 1B. The process and sub-processes of FIG. 2 are computerized processes performed by the system of the main server 110, including the processors of the CPU 112. The aforementioned processes and sub-processes can be performed manually, for example in real time.

The process begins at a START block 202, where a configuration file, e.g., file 180 (FIG. 1B) for the surgeon or doctor performing the procedure in the operating room 55 using the monitors 106 is obtained, edited, revised, or augmented with the necessary windows the surgeon wants to view, for the particular procedure. The desired windows, to be displayed on the monitors 106, for example, are on a whitelist, while windows that the surgeon does not want displayed on the monitors 106, for example, are provided in a blacklist.

The process moves to block 204, where the configuration file for the doctor for example, for the procedure being performed is obtained by the CAS 52. Moving to block 206, the windows displayed by the control room monitors 100 are analyzed against the at least one configuration file for corresponding windows. Example processes for determining the aforementioned correspondence are shown at blocks 208 and 209, to which the process moves. Either or both of the processes of blocks 208 and 209 may be used.

Moving to block 208 (formed by blocks 208a and 208b), a whitelist from the surgeon's configuration file 180 is applied to determine the correspondence of the windows. At block 208a, the windows of the control room monitors 100 are matched with the windows of the whitelist from the doctor's configuration file 180 FIG. 1B). The windows on the control room monitors 100, which match those of the whitelist, are cloned or duplicated, for example, by the cloning module 131 and/or data representative thereof, is sent to the monitors 106 in the operating room 55, at block 208b. The cloned or otherwise duplicated windows are now rendered to and displayed on the monitors 106 in the operating room 55, for use by the surgeon 57, at block 210.

Returning to block 206, and moving to block 209 (formed by blocks 209a and 209b), the blacklist from the surgeon's configuration file 180, is applied to determine the correspondence of the windows. At block 209a, the windows of the control room monitors 100 are matched with the windows of the blacklist from the doctor's (surgeon's)configuration file 180. The windows on the control room monitors 100, which match those of the blacklist are not cloned or duplicated, for example, by the cloning module 131, but rather, the non-blacklisted windows displayed on the monitors 100 of the CAS are cloned or duplicated, at block 209b.

From blocks 208b and 209b, the cloned or otherwise duplicated windows and/or data representative thereof is sent to the monitors 106 in the operating room 55, so as to be rendered for display on the monitors, at block 210. The process moves to block 212, where the cloned windows are displayed on the monitors 106 in the operating room 55, for use by the surgeon 57.

From block 212, the process moves to block 214, where it ends. The process may be repeated for as long as desired by the CAS 52 and the surgeon 57.

Figure 3:
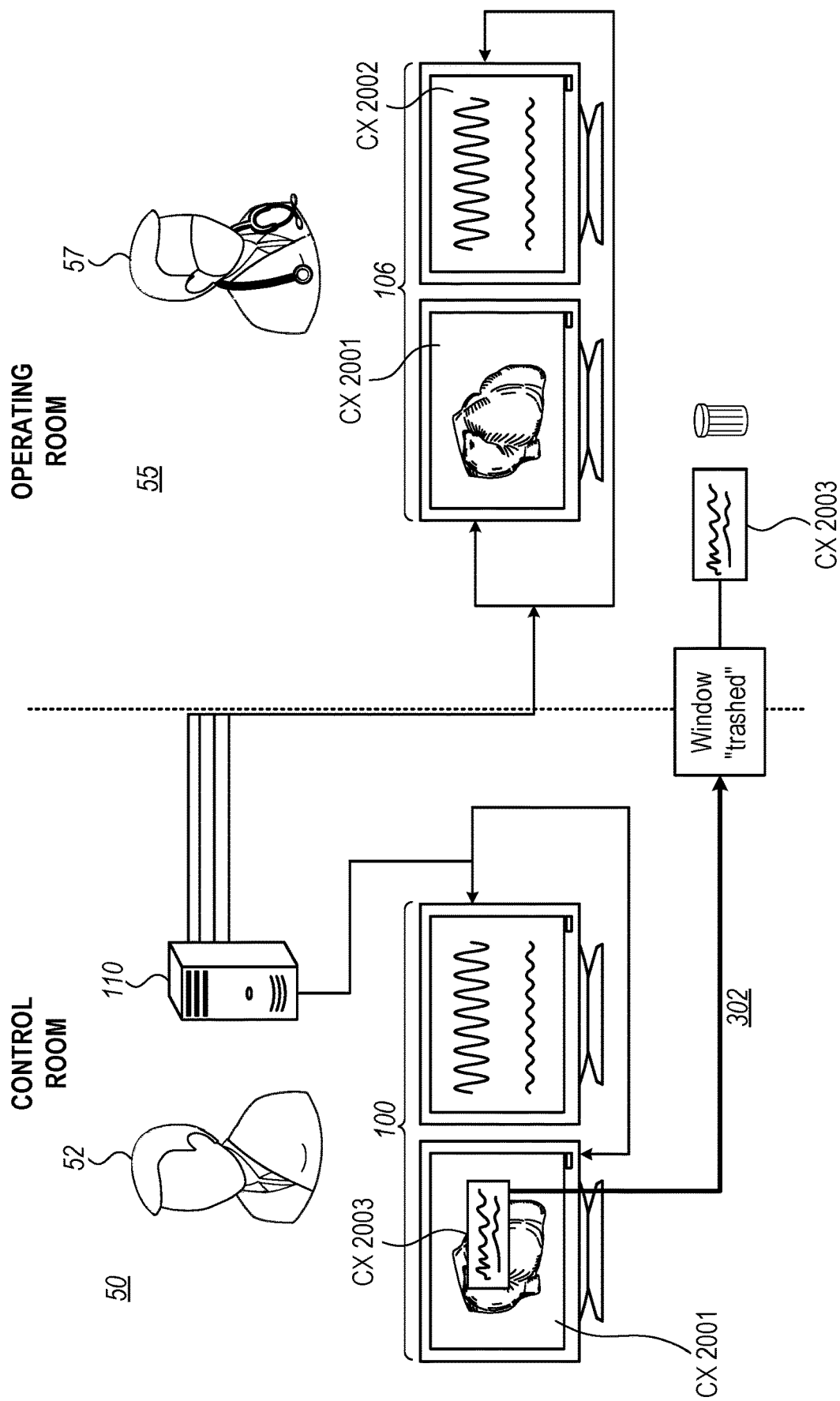
FIG. 3 is a diagram of the system showing the example processes of FIG. 2 performed thereon, in accordance with an example of the disclosed subject matter.

FIG. 3 shows example operations of the process of FIG. 2. Reference is also made to FIGS. 1A and 1B when discussing FIG. 3. In the control room 50, the monitors 100 of the CAS are displaying windows CX2001, CX2002 and CX2003.

When the whitelist, for example, configuration file 180, File 1001 for Doctor A (DRA), of the configuration files 120 of FIG. 1B, is applied, as described for blocks 208a and 208b, windows CX2001 and CX2002 from the whitelist, match the windows CX2001 and CX2002 displayed on the monitors 100 of the CAS 52 in the control room 50. Accordingly, windows CX2001 and CX2002 are cloned (duplicated) and sent to the operating room 55 monitors 106 for rendering thereto and display thereon, as shown. The window CX2003 is not cloned, and thus not sent to the operating room monitors 106, and, for example, optionally is "trashed", thrown away or otherwise discarded, as shown by the arrow 302.

When the blacklist, for example, configuration file 1001 for Doctor A 180 (FIG. 1B), of the configuration files 120, is applied, as described for blocks 209a and 209b, window CX2003 from the blacklist matches the windows CX2003 displayed on the monitors 100 of the CAS 52 in the control room 50. Accordingly, window CX2003 is not cloned, but windows CX2001 and CX2002, which are displayed on the CAS monitors 100, are cloned (duplicated), and sent to the operating room 55 monitors 106 for rendering thereto, and display thereon, as shown. The window CX2003 is not cloned, and thus not sent to the operating room monitors 106, and, for example, optionally is "trashed", thrown away or otherwise discarded, as shown by the arrow 302.

Typically, the main server 110 comprises a general-purpose computer, which is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Although the examples described herein mainly address computer systems and monitors associated with a CARTO and other medical procedures, the methods and systems described herein can also be used in other applications, such as in other computer operations where the displays of one set of monitor(s) is selectively cloned to another set of monitor(s), with the monitor(s) located at different locations, for different parts of a room, to different, rooms or areas in the same or a different building, at any location in the world.

The aforementioned disclosed subject matter, for example, is also in the form of a computer software product. The product comprises, for example, a tangible non-transitory computer-readable medium in which program instructions are stored, which instructions, when read by a processor, cause the processor to selectively clone computer display monitors from a first one or more monitors, associated with an operator, to a second one or more monitors, associated with a surgeon.

EXAMPLE 1

A method is for selectively cloning computer display monitors (100, 106) from a first one or more monitors (100) associated with an operator (52), to a second one or more monitors (106) associated with a surgeon (57). The method comprises: obtaining at least one configuration comprising one or more Graphical User Interface (GUI) elements, which are to be rendered to the second one or more monitors (106) or not rendered to the second one or more monitors (106); analyzing the Graphical User Interface (GUI) elements displayed by the first one or more monitors (100) against the at least one configuration (120) for corresponding Graphical User Interface (GUI) elements; cloning corresponding Graphical User Interface (GUI) elements; and, sending data representative of the cloned corresponding Graphical User Interface (GUI) elements to the second one or more monitors (106) for display on the second one or more monitors (106).

EXAMPLE 2

The method according to Example 1 additionally comprising: displaying on the second one or more monitors (106) the cloned corresponding Graphical User Interface (GUI) elements.

EXAMPLE 3

The method according to Example 1 or Example 2, wherein the Graphical User Interface (GUI) elements comprise windows.

EXAMPLE 4

The method according to any one of Examples 1 through 3, wherein the configuration (120) comprises at least one configuration file (180).

EXAMPLE 5

The method according to any one of Examples 1 through 4, wherein the corresponding GUI elements comprise the windows displayed on the first one or more monitors (100) which match the windows on a whitelist of the at least one configuration (120).

EXAMPLE 6

The method according to any one of Examples 1 through 5, wherein the corresponding GUI elements comprise the GUI elements displayed on the first one or more monitors (100) which do not match the GUI elements on a blacklist of the at least one configuration (120).

EXAMPLE 7

The method according to any one of Examples 1 through 6, wherein the first one or more monitors (100) are in a control room (50) and the second one or more monitors (106) are in an operating room (55).

EXAMPLE 8

A system is for selectively cloning computer display monitors (100, 106). The system comprises: a computer (110) in communication with a first one or more monitors (100) associated with an operator (52), and a second one or more monitors (106) associated with a surgeon (57), the computer (110) comprising: storage media (114) for storing computer components; and, at least one processor (112) for executing the computer components. The computer components comprise: a first computer component (120) for storing at least one configuration comprising one or more Graphical User Interface (GUI) elements, which are to be rendered to the second one or more monitors (106) or not rendered to the second one or more monitors (106); a second computer component (112) for analyzing GUI elements displayed by a the first one or more monitors (100) associated with the operator (52), against the at least one configuration, for corresponding GUI elements; and, a third computer component (131) for cloning the corresponding GUI elements and sending data representative of the cloned corresponding GUI elements to a second one or more monitors (106) associated with the surgeon (57) for display on the second one or more monitors (106).

EXAMPLE 9

The system according to Example 8, wherein the corresponding GUI elements for the second computer component (112) comprise windows displayed on the first one or more monitors (100) which match the windows on a whitelist of the at least one configuration (120).

EXAMPLE 10

The system according to Example 8 or Example 9, wherein the at least one configuration (120) comprises at least one configuration file (180).

EXAMPLE 11

The system according to any one of Examples 8 through 10, wherein the corresponding GUI elements for the second computer component (112) comprise windows displayed on the first one or more monitors (100) which do not match the windows on a blacklist of the at least one configuration (120).

EXAMPLE 12

The system according to any one of Examples 8 through 11, wherein the at least one configuration (120) comprises at least one configuration file (180).

EXAMPLE 13

A computer software product, the product comprising a tangible non-transitory computer-readable medium in which program instructions are stored, which instructions, when read by a processor (112), cause the processor (112) to selectively clone computer display monitors from a first one or more monitors (100), associated with an operator (52), to a second one or more monitors (106), associated with a surgeon (57), wherein the instructions cause the processor (112) to: obtain at least one configuration comprising one or more Graphical User Interface (GUI) elements, which are to be rendered to the second one or more monitors (106) or not rendered to the second one or more monitors (106); analyze the Graphical User Interface (GUI) elements displayed by the first one or more monitors (100) against the at least one configuration for corresponding Graphical User Interface (GUI) elements; clone corresponding Graphical User Interface (GUI) elements; and, send data representative of the cloned corresponding Graphical User Interface (GUI) elements to the second one or more monitors (106) for display on the second one or more monitors.

EXAMPLE 14

The computer software product according to Example 13, wherein the instructions additionally cause the processor (112) to: display on the second one or more monitors (106) the cloned corresponding GUI elements.

EXAMPLE 15

The computer software product according to Example 13 or Example 14, wherein the at least one configuration (120) comprises at least one configuration file (180).

EXAMPLE 16

The computer software product according to any one of Examples 13 through 15, wherein the corresponding GUI elements comprise windows displayed on the first one or more monitors (100) which match the windows on a whitelist of the at least one configuration (120).

EXAMPLE 17

The computer software product according to any of Examples 13 through 16, wherein the corresponding GUI elements comprise windows displayed on the first one or more monitors (100) which do not match the windows on a blacklist of the at least one configuration (120).

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for selectively cloning computer display monitors, the system comprising:
   a computer in communication with a first one or more monitors associated with an operator, and a second one or more monitors associated with a surgeon, the computer comprising:
   storage media for storing computer components; and
   at least one processor for executing the computer components, the computer components comprising:
      a first computer component for storing at least one configuration comprising one or more Graphical User Interface (GUI) elements, which are to be rendered to the second one or more monitors or not rendered to the second one or more monitors;
      a second computer component for analyzing GUI elements displayed by a the first one or more monitors associated with the operator, against the at least one configuration, for corresponding GUI elements; and
      a third computer component for cloning the corresponding GUI elements and sending data representative of the cloned corresponding GUI elements to a second one or more monitors associated with the surgeon for display on the second one or more monitors.

2. The system of claim 1, wherein the corresponding GUI elements for the second computer component comprise windows displayed on the first one or more monitors which match the windows on a whitelist of the at least one configuration.

3. The system of claim 1, wherein the at least one configuration comprises at least one configuration file.

4. The system of claim 1, wherein the corresponding GUI elements for the second computer component comprise windows displayed on the first one or more monitors which do not match the windows on a blacklist of the at least one configuration.

5. The system of claim 4, wherein the at least one configuration comprises at least one configuration file.

6. A computer software product, the product comprising a tangible non-transitory computer-readable medium in which program instructions are stored, which instructions, when read by a processor, cause the processor to selectively clone computer display monitors from a first one or more monitors, associated with an operator, to a second one or more monitors, associated with a surgeon, wherein the instructions cause the processor to:
- obtain at least one configuration comprising one or more Graphical User Interface (GUI) elements, which are to be rendered to the second one or more monitors or not rendered to the second one or more monitors;
- analyze the Graphical User Interface (GUI) elements displayed by the first one or more monitors against the at least one configuration for corresponding Graphical User Interface (GUI) elements;
- clone corresponding Graphical User Interface (GUI) elements; and
- send data representative of the cloned corresponding Graphical User Interface (GUI) elements to the second one or more monitors for display on the second one or more monitors.

7. The computer software product of claim 6, wherein the instructions additionally cause the processor to:
- display on the second one or more monitors the cloned corresponding GUI elements.

8. The computer software product of claim 6, wherein the at least one configuration comprises at least one configuration file.

9. The computer software product of claim 6, wherein the corresponding GUI elements comprise windows displayed on the first one or more monitors which match the windows on a whitelist of the at least one configuration.

10. The computer software product of claim 6, wherein the corresponding GUI elements comprise windows displayed on the first one or more monitors which do not match the windows on a blacklist of the at least one configuration.

11. A method for selectively cloning computer display monitors from a first one or more monitors associated with an operator, to a second one or more monitors associated with a surgeon, the method comprising:
- obtaining at least one configuration comprising one or more Graphical User Interface (GUI) elements, which are to be rendered to the second one or more monitors or not rendered to the second one or more monitors;
- analyzing the Graphical User Interface (GUI) elements displayed by the first one or more monitors against the at least one configuration for corresponding Graphical User Interface (GUI) elements;
- cloning corresponding Graphical User Interface (GUI) elements; and
- sending data representative of the cloned corresponding Graphical User Interface (GUI) elements to the second one or more monitors for display on the second one or more monitors.

12. The method of claim 11, additionally comprising:
- displaying on the second one or more monitors the cloned corresponding Graphical User Interface (GUI) elements.

13. The method of claim 11, wherein the Graphical User Interface (GUI) elements comprise windows.

14. The method of claim 11, wherein the configuration comprises at least one configuration file.

15. The method of claim 11, wherein the corresponding GUI elements comprise the windows displayed on the first one or more monitors which match the windows on a whitelist of the at least one configuration.

16. The method of claim 11, wherein the corresponding GUI elements comprise the GUI elements displayed on the first one or more monitors which do not match the GUI elements on a blacklist of the at least one configuration.

17. The method of claim 11, wherein the first one or more monitors are in a control room and the second one or more monitors are in an operating room.

* * * * *